US008515540B2

(12) United States Patent
Leigh et al.

(10) Patent No.: US 8,515,540 B2
(45) Date of Patent: Aug. 20, 2013

(54) FEEDTHROUGH HAVING A NON-LINEAR CONDUCTOR

(75) Inventors: Charles Roger Aaron Leigh, East Ryde (AU); Mark Alan Von Huben, Waverton (AU); Grahame Michael David Walling, Dee Why (AU)

(73) Assignee: Cochlear Limited, Macquarie University, NSW (AU)

( * ) Notice: Subject to any disclaimer, the term of this patent is extended or adjusted under 35 U.S.C. 154(b) by 178 days.

(21) Appl. No.: 13/034,470

(22) Filed: Feb. 24, 2011

(65) Prior Publication Data

US 2012/0221078 A1  Aug. 30, 2012

(51) Int. Cl.
*A61N 1/00* (2006.01)
(52) U.S. Cl.
USPC .......................................................... 607/36
(58) Field of Classification Search
USPC .................. 607/36, 37, 57; 429/181; 29/831
See application file for complete search history.

(56) References Cited

U.S. PATENT DOCUMENTS

| 4,441,202 A | 4/1984 | Tong et al. |
| 4,515,158 A | 5/1985 | Patrick et al. |
| 4,532,930 A | 8/1985 | Crosby et al. |
| 4,611,596 A | 9/1986 | Wasserman |
| 4,617,913 A | 10/1986 | Eddington |
| 4,847,617 A | 7/1989 | Silvian |
| 5,046,242 A | 9/1991 | Kuzma |
| 5,207,218 A | 5/1993 | Carpentier et al. |
| 5,271,397 A | 12/1993 | Seligman et al. |
| 5,274,711 A | 12/1993 | Rutledge et al. |
| 5,403,262 A | 4/1995 | Gooch |
| 5,412,748 A | 5/1995 | Furuyama et al. |
| 5,601,617 A | 2/1997 | Loeb et al. |
| 5,609,616 A | 3/1997 | Schulman et al. |
| 5,626,629 A | 5/1997 | Faltys et al. |
| 5,649,970 A | 7/1997 | Loeb et al. |
| 5,653,742 A | 8/1997 | Parker et al. |
| 5,687,282 A | 11/1997 | Kerkhof |
| 5,741,313 A | 4/1998 | Davis et al. |
| 5,750,926 A | 5/1998 | Schulman et al. |

(Continued)

FOREIGN PATENT DOCUMENTS

| AU | 2005202733 | 1/2006 |
| EP | 0247649 | 12/1987 |

(Continued)

OTHER PUBLICATIONS

International Search Report and Written Opinion for International Application No. PCT/IB2012/050840 mailed Oct. 25, 2012 (9 pages).

(Continued)

*Primary Examiner* — George Manuel
*Assistant Examiner* — Robert N Wieland
(74) *Attorney, Agent, or Firm* — Kilpatrick, Townsend & Stockton, LLP

(57) ABSTRACT

The implantable medical device including a hermetic enclosure including at least one feedthrough having at least one electrically conductive path through the feedthrough. The at least one feedthrough includes an insulator having an entry face and an exit face, and at least one non-linear conductor is configured to extend, within the insulator, from the entry face to the exit face to provide the conductive path, wherein the entry and exit faces are not substantially parallel opposite faces of the insulator.

28 Claims, 8 Drawing Sheets

(56) References Cited

U.S. PATENT DOCUMENTS

| | | |
|---|---|---|
| 5,776,179 A | 7/1998 | Ren et al. |
| 5,786,439 A | 7/1998 | Van Antwerp et al. |
| 5,824,022 A | 10/1998 | Zilberman et al. |
| 5,833,714 A | 11/1998 | Loeb |
| 5,853,424 A | 12/1998 | Rise |
| 5,876,424 A | 3/1999 | O'Phelan et al. |
| 5,895,416 A | 4/1999 | Barreras, Sr. et al. |
| 5,909,497 A | 6/1999 | Alexandrescu |
| 6,115,478 A | 9/2000 | Schneider |
| 6,116,413 A | 9/2000 | Tabor et al. |
| 6,198,971 B1 | 3/2001 | Leysieffer |
| 6,230,057 B1 | 5/2001 | Chow et al. |
| 6,304,786 B1 | 10/2001 | Heil, Jr. et al. |
| 6,304,787 B1 | 10/2001 | Kuzma et al. |
| 6,321,126 B1 | 11/2001 | Kuzma |
| 6,334,072 B1 | 12/2001 | Leysieffer |
| 6,354,299 B1 | 3/2002 | Fischell et al. |
| 6,366,863 B1 | 4/2002 | Bye et al. |
| 6,421,569 B1 | 7/2002 | Treaba et al. |
| 6,463,328 B1 | 10/2002 | John |
| 6,497,729 B1 | 12/2002 | Moussy et al. |
| 6,537,200 B2 | 3/2003 | Leysieffer et al. |
| 6,565,503 B2 | 5/2003 | Leysieffer et al. |
| 6,575,894 B2 | 6/2003 | Leysieffer et al. |
| 6,594,525 B1 | 7/2003 | Zierhofer |
| 6,697,674 B2 | 2/2004 | Leysieffer |
| 6,721,602 B2 | 4/2004 | Engmark et al. |
| 6,751,505 B1 | 6/2004 | Van Den Honert et al. |
| 6,778,040 B2 | 8/2004 | Kim |
| 6,778,858 B1 | 8/2004 | Peeters |
| 6,879,693 B2 | 4/2005 | Miller |
| 6,916,291 B2 | 7/2005 | Givens et al. |
| 7,110,819 B1 | 9/2006 | O'Hara |
| 7,120,992 B2 | 10/2006 | He et al. |
| 7,164,572 B1 | 1/2007 | Burdon et al. |
| 7,171,272 B2 | 1/2007 | Blamey et al. |
| 7,181,297 B1 | 2/2007 | Pluvinage et al. |
| 7,211,184 B2 | 5/2007 | Webster et al. |
| 7,218,971 B2 | 5/2007 | Heil, Jr. et al. |
| 7,251,530 B1 | 7/2007 | Overstreet et al. |
| 7,272,446 B2 | 9/2007 | Parker et al. |
| 7,317,944 B1 | 1/2008 | Overstreet |
| 7,328,151 B2 | 2/2008 | Muesch |
| 7,396,265 B2 | 7/2008 | Darley et al. |
| 7,421,298 B2 | 9/2008 | Daly |
| 7,920,925 B2 | 4/2011 | Overstreet et al. |
| 2001/0031909 A1 | 10/2001 | Faltys et al. |
| 2001/0050837 A1 | 12/2001 | Stevenson et al. |
| 2002/0107555 A1 | 8/2002 | Rusin et al. |
| 2002/0176584 A1 | 11/2002 | Kates |
| 2003/0109903 A1 | 6/2003 | Berrang et al. |
| 2003/0199950 A1 | 10/2003 | Stolz et al. |
| 2003/0233133 A1 | 12/2003 | Greenberg et al. |
| 2004/0098063 A1 | 5/2004 | Goelz |
| 2004/0127968 A1 | 7/2004 | Kuzma et al. |
| 2004/0147974 A1 | 7/2004 | Engmark et al. |
| 2004/0147992 A1 | 7/2004 | Bluger et al. |
| 2004/0176815 A1 | 9/2004 | Janzig et al. |
| 2004/0191621 A1 | 9/2004 | Heller, Jr. |
| 2006/0004432 A1 | 1/2006 | Parker et al. |
| 2006/0025833 A1 | 2/2006 | Daly |
| 2007/0127745 A1 | 6/2007 | Gibson et al. |
| 2007/0236861 A1 | 10/2007 | Burdon et al. |
| 2007/0277374 A1* | 12/2007 | Suaning ................. 29/831 |
| 2008/0119910 A1 | 5/2008 | Daly |
| 2008/0209723 A1 | 9/2008 | Darley et al. |
| 2009/0034769 A1 | 2/2009 | Darley et al. |
| 2009/0118795 A1 | 5/2009 | Ibrahim et al. |
| 2009/0192578 A1 | 7/2009 | Biggs |
| 2009/0204177 A1 | 8/2009 | Parker et al. |
| 2009/0207550 A1 | 8/2009 | Feichtinger et al. |
| 2010/0030296 A1 | 2/2010 | Rundle et al. |
| 2011/0125210 A1* | 5/2011 | Francis et al. ............. 607/37 |

FOREIGN PATENT DOCUMENTS

| | | |
|---|---|---|
| EP | 0282336 | 9/1988 |
| EP | 0124930 | 6/1990 |
| EP | 0714317 | 4/2002 |
| JP | 61001200 | 1/1986 |
| JP | 63242252 | 10/1988 |
| JP | 8501241 | 2/1996 |
| JP | 10508442 | 8/1998 |
| JP | 11513539 | 11/1999 |
| JP | 2000509566 | 7/2000 |
| WO | WO-9324176 | 12/1993 |
| WO | WO-9501709 | 1/1995 |
| WO | WO-9612383 | 4/1996 |
| WO | WO-9626673 | 9/1996 |
| WO | WO-9709863 | 3/1997 |
| WO | WO-9738653 | 10/1997 |
| WO | WO-9743871 | 11/1997 |
| WO | WO-9748447 | 12/1997 |
| WO | WO-9965276 | 12/1999 |
| WO | WO-0103622 | 1/2001 |
| WO | WO-0119304 | 3/2001 |
| WO | WO-0199470 | 12/2001 |
| WO | WO-0217679 | 2/2002 |
| WO | WO 2006/081361 | 8/2006 |
| WO | WO 2009/003235 | 1/2009 |
| WO | WO 2009/073476 | 11/2009 |

OTHER PUBLICATIONS

CA Examiner's report, CA Application No. 2,419,321, mailed May 29, 2007.

CA Examiner's report, CA Application No. 2,419,321, mailed Dec. 10, 2008.

Specialty Coating Systems: Rubber/Silicone, *Specialty Coating Systems*, (Webpage), www.scscoatings.com/1_parylene_applications/rubber-silicone.cfm, accessed via Internet Archive Wayback Machine (archive.org), available Nov. 24, 2005 (based on records of Internet Archive).

European Search Report, EP Application No. 01959971, mailed Aug. 11, 2005.

First European Examiner's Report, EP 01959971.1 mailed Nov. 23, 2005.

Notice of Reasons for Rejection, JP2002-561453, mailed Jun. 16, 2009.

Office Action, JP 2003-509823, mailed Oct. 28, 2008.

Office Action, JP 2003-509823, mailed Aug. 19, 2008.

Office Action, JP 2003-509823, mailed Jan. 15, 2008.

Abbas, et al., "Electrically Evoked Compound Action Potentiais Recorded from Subjects Who Use the Nucieus C12M Device", Gantz et al. *Seventh Symposium on Cochlear Implants in Children Ann. Otol. Rhinol. Laryngol. Suppl. 185* Dec. 2000 , 185, 6-9.

Examiner's First Report, AU2002311095, mailed Sep. 26, 2006.

Notice of Acceptance AU2002311095, mailed Jun. 16, 2008.

Baumgarte, et al., "A Nonlinear Psychoacoustic Model Applied to the ISO MPEG Layer 3-coder", *Proceedings of the 99th Convention Aud. Eng. Soc.*, New York . Institut for Theoretische Nachrichtentechnik und Informationsverarbeitung, Universitat Hannover. Germany Oct. 1995.

Cohen, et al., "Spatial spread of neural excitation in cochlear implant recipients:—comparison of improved ECAP method and psychophysical forward masking", *Hearing Research* May 2003 , vol. 179, pp. 72-87.

Cohen, et al., "Spatial spread of neural excitation: comparison of compound action potential and forward-masking data in cochlear implant recipients", *International Journal of Audiology* 2004 , vol. 43, pp. 346-355.

Edler, et al., "ASAC Analaysis/Synthesis Audio Codec for Very Low Bit rates", *Proceedings of the 100th Conv. Aud. Eng. Soc. Institit for theoretische Nachrichtentechnik und Informationsverarbeitung,* Universitat Hannover , Germany May 1996.

Miller, et al., "An Improved Method of Reducing Stimulus Artifact in the Electrically Evoked whole Nerve Potential", *Ear & Hearing* Aug. 2000, 21(4): 280-290.

Nogueira, et al., "A Psychoacoustic 'NofM'—Type Speech Coding Strategy for Cochlear Implants", *EURASIP journal on Applied Signal Processing* 2005, 3044-3059.

International Preliminary Examination Report, PCT/AU2001/01032, mailed Apr. 2, 2002.

International Search Report, PCT/AU2001/01032, mailed Oct. 5, 2001.

Communication pursuant to Article 94(3), EPC European Application No. 02734913.3 mailed on Sep. 15, 2010 (4 pages).

* cited by examiner

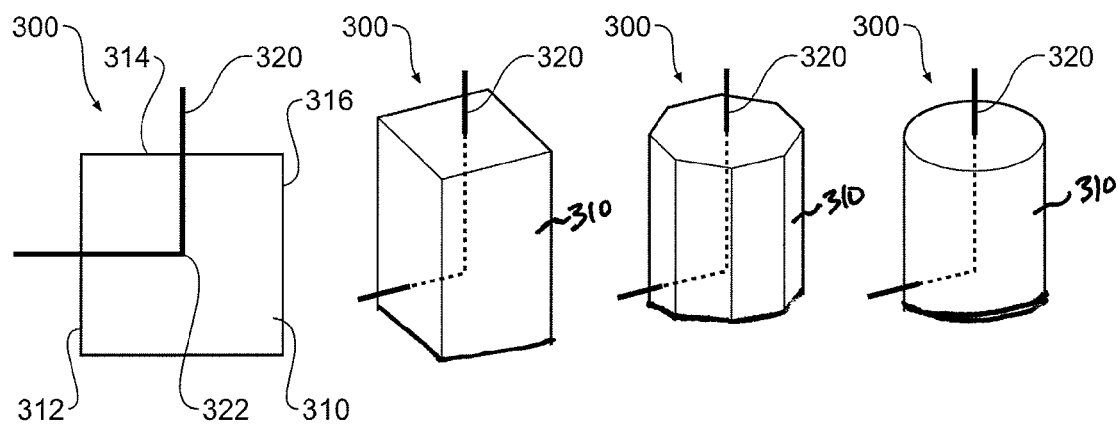
FIG. 3A  FIG. 3B  FIG. 3C  FIG. 3D
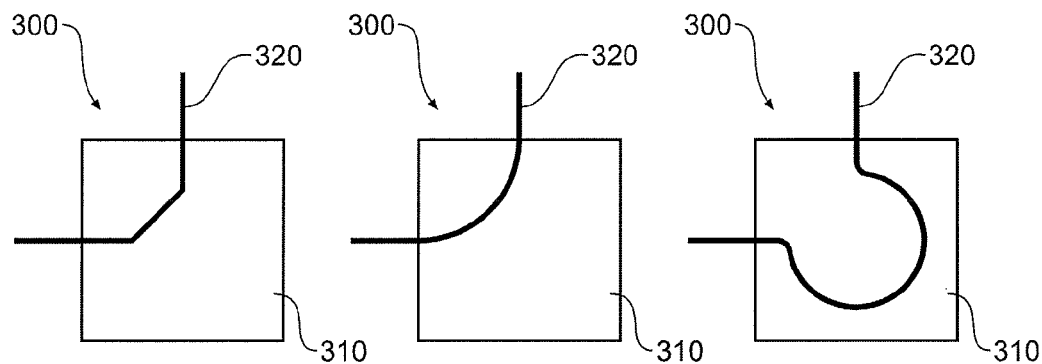
FIG. 4A  FIG. 4B  FIG. 4C
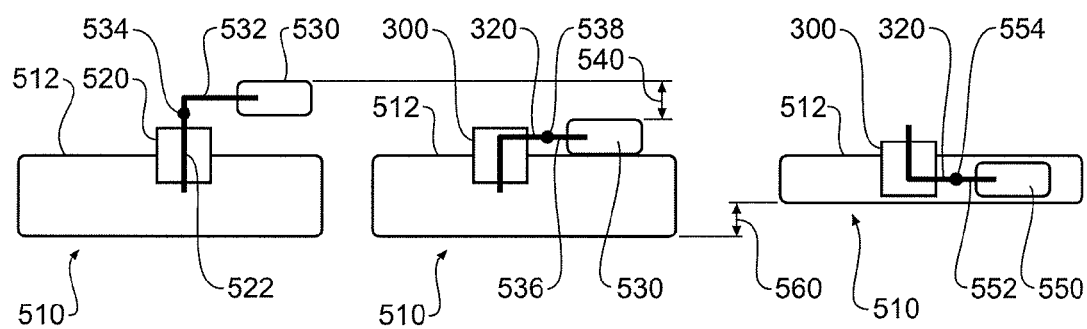
FIG. 5A
(PRIOR ART)
FIG. 5B  FIG. 5C

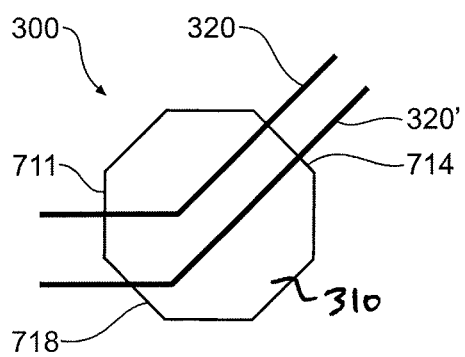
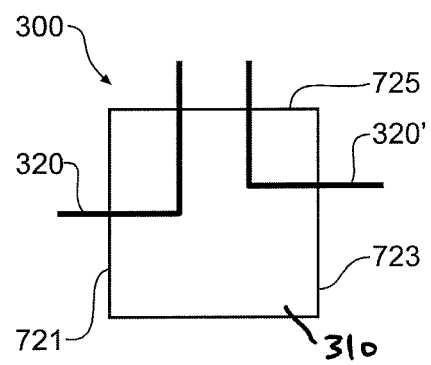
FIG. 7A  FIG. 7B
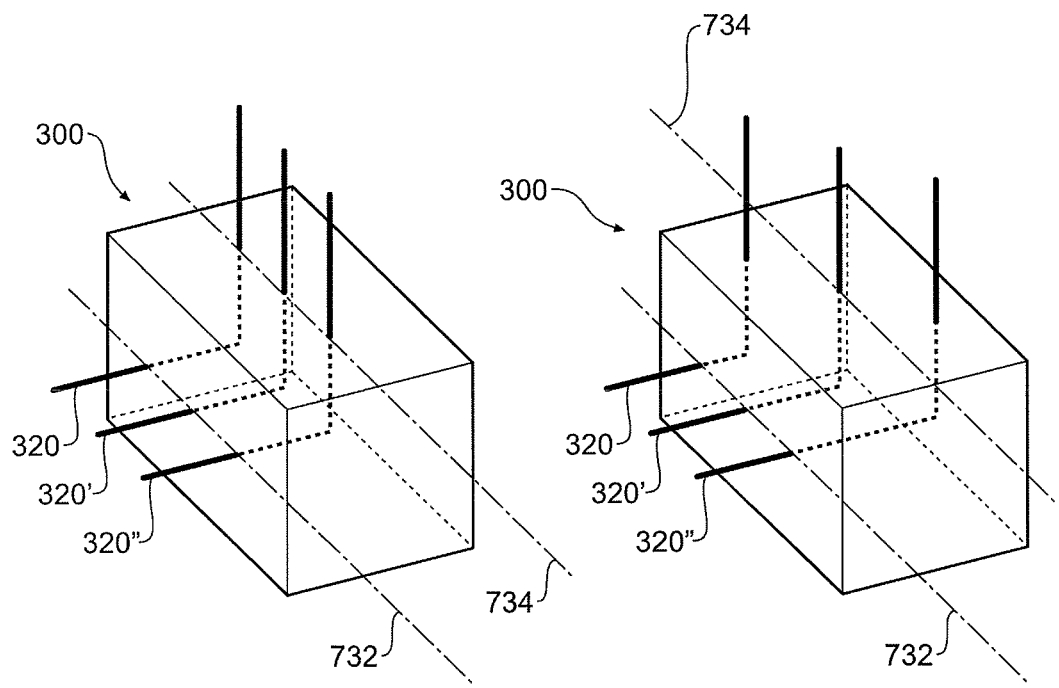
FIG. 7C  FIG. 7D

FEEDTHROUGH HAVING A NON-LINEAR CONDUCTOR

BACKGROUND

1. Field of the Invention

The present invention is generally directed to feedthroughs for implantable medical devices, and more particularly, to a feedthrough having a non-linear conductor.

2. Related Art

There are several types of implantable medical devices (sometimes referred to as "medical implants" herein) that are designed to be temporarily or permanently implanted within a patient or recipient ("recipient" herein). Implantable medical devices may be partially implantable, including both one or more implantable components and one or more external components, or completely implantable. Such implantable medical devices perform one or more of a variety of therapeutic functions such as stimulate nerve or other tissue, monitor biological functions or physiological parameters, transfer materials between the exterior and interior of the recipient, perform functions previously performed by organs or other biological systems, etc.

Depending on the application and/or intended function, an implantable component of a partially or completely implantable medical device can be implanted directly underneath the skin or deep within a recipient adjacent to or in an organ or bone of the recipient. In order to minimize the amount of surgery and/or discomfort to the recipient, it is generally desirable to make implantable components as thin and compact as possible. This is of even greater importance when the recipients are young children.

Cochlear implants use direct electrical stimulation of auditory nerve cells to bypass absent or defective hair cells that normally transduce acoustic vibrations into neural activity. Such devices generally use an electrode array inserted into the scala tympani of the cochlea so that the electrodes can selectively stimulate cells of the recipient's auditory nerve.

Auditory brain stimulators are used to treat a smaller number of recipients with bilateral degeneration of the auditory nerve. For such recipients, the auditory brain stimulator provides stimulation of the cochlear nucleus in the brainstem, typically with a planar electrode array; that is, an electrode array in which the electrode contacts are disposed on a two dimensional surface that can be positioned proximal to the brainstem.

Implantable medical devices, such as those described above, include one or more functional components located within an implantable housing of an implantable component. As used herein, a "functional component" refers to any mechanical, eletro-mechanical, or electronic component of an implantable medical device. Typically, at least some of the functional components, such as electronic components, incorporate non-biocompatible materials (e.g. copper, lead, ferrite, etc.) and thus these components must be located in a hermetic enclosure. This hermetic enclosure protects the body from any non-biocompatible materials contained in an implantable component and protects the electronic assembly from body fluids. A breakdown in the hermetic enclosure can lead to adverse reactions in the recipient (e.g., inflammation or cytotoxicity) or the device (e.g., malfunctions) and necessitate removal of one or more implantable components, or can cause a recipient to stop using the device to avoid the above or other adverse effects.

In certain implantable medical devices, an electrically conductive path is provided through a wall of the hermetic enclosure to allow electrical signals to be communicated between components within the hermetic enclosure and components outside of the hermetic enclosure. For example, in a cochlear implant, electrical stimulation pulses may be provided from within a hermetic enclosure to electrodes disposed outside of the hermetic enclosure that are used to directly stimulate auditory nerve cells. Electrical feedthrough arrangements typically comprise one or more electrically conductive pins mounted in a glass or ceramic insulator to electrically insulate the pin from the container or housing.

SUMMARY

In one aspect of the present invention, an implantable medical device is disclosed. The implantable medical device comprises a hermetic enclosure including at least one feedthrough having at least one electrically conductive path through the feedthrough. The at least one feedthrough comprises an insulator having an entry face and an exit face, and at least one non-linear conductor configured to extend, within the insulator, from the entry face to the exit face to provide the conductive path, wherein the entry and exit faces are not substantially parallel opposite faces of the insulator.

In another aspect of the present invention a cochlear implant system is disclosed. The cochlear implant system comprises an electrode array, and an electronics module comprising a hermetic enclosure encasing one or more functional components and including at least one feedthrough having at least one electrically conductive path through the feedthrough configured to electrically connect the functional components to the electrode array. The at least one feedthrough comprises an insulator having an entry face and an exit face; and at least one non-linear conductor configured to extend, within the insulator, from the entry face to the exit face to provide the conductive path, wherein the entry and exit faces are not substantially parallel opposite faces of the insulator.

In another aspect of the present invention, a method of forming a feedthrough for an implantable medical device is disclosed. The method comprises forming at least one non-linear conductor, and encapsulating a portion of the non-linear conductor with an insulating material to form a contiguous insulator having entry and exit faces that are not substantially parallel opposite faces of the insulator, wherein that the non-linear conductor is configured to extend, within the insulator, from the entry face to the exit face. The method further comprises hermetically sealing the portion of the non-linear conductor encapsulated in the insulator.

BRIEF DESCRIPTION OF THE DRAWINGS

Illustrative embodiments of the present invention are described herein with reference to the accompanying drawings, in which:

FIGS. 3A to 3D are schematic diagrams of a feedthrough in accordance with embodiments of the present invention;

FIGS. 4A to 4C illustrate various feedthrough in accordance with alternative embodiments of the invention;

FIG. 5A is a schematic diagram of a conventional medical implant;

FIGS. 5B and 5C are schematic diagrams of medical implants each having a feedthrough in accordance with embodiments of the present invention;

FIGS. 7A to 7D are schematic diagrams of feedthroughs comprising a plurality of conductors in accordance with embodiments of the present invention;

DETAILED DESCRIPTION

Aspects of the present invention are generally directed to electrical feedthrough arrangements for use in implantable medical devices. In certain embodiments of the invention, the electrical feedthroughs enable the production of thinner or more compact implantable components of implantable medical devices. The term "feedthrough" as used herein refers to the provision of at least one electrically conductive path extending through an insulator (or insulative member). In some embodiments, the electrically conductive path electrically connects the functional components located in the interior of a hermetically sealed enclosure (i.e., a container, housing, etc.) of a device to functional components external to the hermetic enclosure. That is, in some embodiments, the conductor provides an electrically conductive path from one side of the insulator to another side of the insulator.

Embodiments are described herein primarily in connection with one type of stimulating implantable medical device, namely a cochlear implant. However, it will be understood that feedthroughs in accordance with embodiments of the present invention may be used in other types of implantable medical devices, including other types of hearing prostheses. Hearing prostheses include but are not limited to hearing aids, auditory brain stimulators, and cochlear prostheses (referred to as "cochlear implants" herein).

Figure 1:
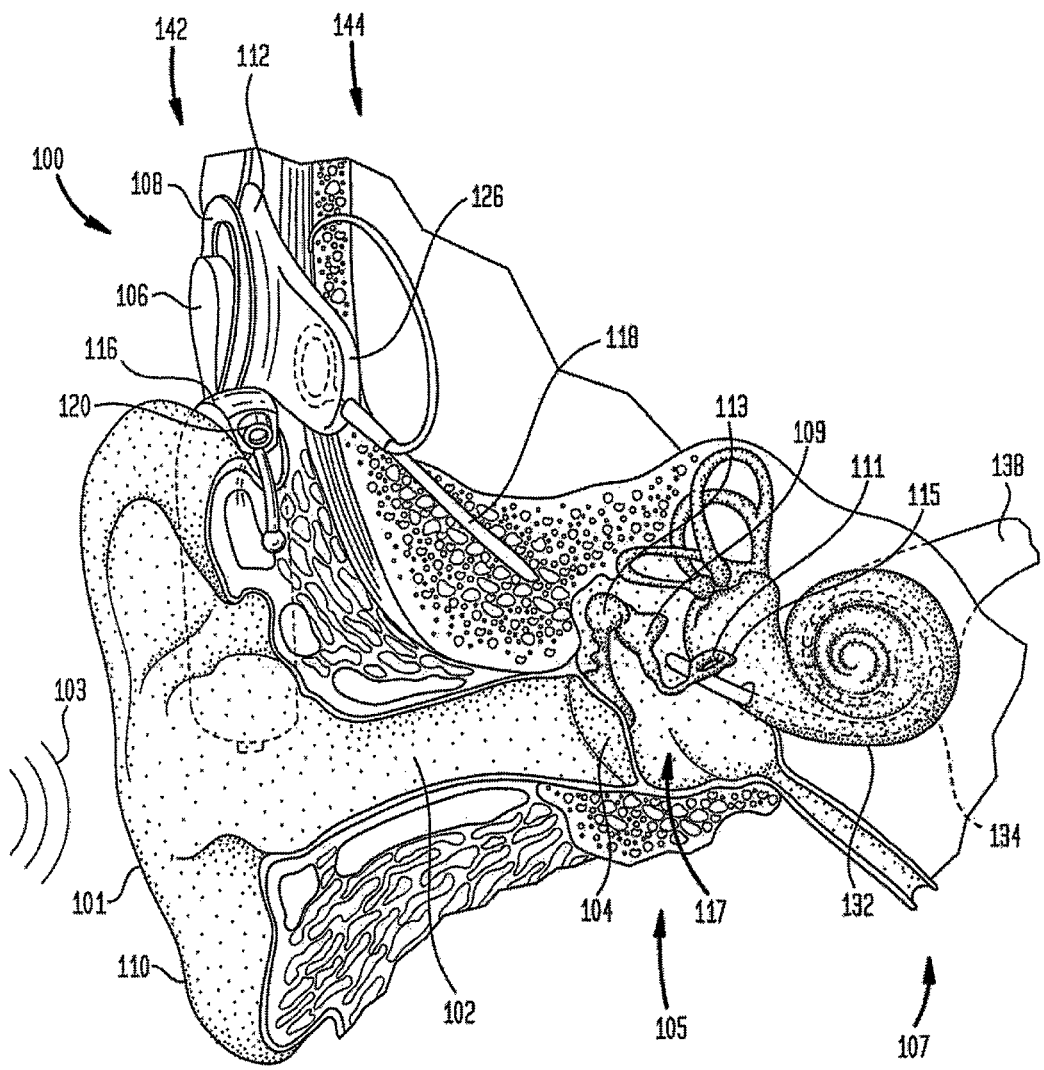
FIG. 1 is a schematic diagram of a cochlear implant in which embodiments of the present invention may be implemented.

FIG. 1 is a perspective view of an exemplary cochlear implant system 100 in which embodiments of the present invention may be implemented. The relevant components of outer ear 101, middle ear 105 and inner ear 107 are described below. An acoustic pressure or sound wave 103 is collected by outer ear 101 (e.g., the auricle) and channeled into and through ear canal 102. Disposed across the distal end of ear canal 102 is a tympanic membrane 104 which vibrates in response to sound wave 103. This vibration is coupled to oval window or fenestra ovalis 115 through three bones of middle ear 105, collectively referred to as the ossicles 117 and comprising the malleus 113, the incus 109 and the stapes 111. Bones 113, 109 and 111 of middle ear 105 serve to filter and amplify sound wave 103, causing oval window 115 to articulate, or vibrate. Such vibration sets up waves of fluid motion within cochlea 132. Such fluid motion, in turn, activates tiny hair cells (not shown) that line the inside of cochlea 132. Activation of the hair cells causes appropriate nerve impulses to be transferred through the spiral ganglion cells (not shown) and auditory nerve 138 to the brain (not shown), where they are perceived as sound.

Cochlear implant system 100 comprises external component assembly 142 which is directly or indirectly attached to the body of the recipient, and an internal component assembly 144 which is temporarily or permanently implanted in the recipient. External component assembly 142 typically comprises one or more audio pickups (e.g., microphone(s)) 120 for detecting sound, a speech processing unit 116, a power source (not shown), and an external transmitter unit 106. External transmitter unit 106 comprises an external coil 108 and, in some embodiments, a magnet (not shown) secured directly or indirectly to the external coil 108. Speech processing unit 116 processes the output of audio pickup (e.g., microphone) 120 that is positioned, in the depicted embodiment, by ear 110 of the recipient. Speech processing unit 116 generates coded signals, referred to herein as stimulation data signals, which are provided to external transmitter unit 106 via a cable (not shown). Speech processing unit 116 is, in this illustration, constructed and arranged so that it can fit behind outer ear 101 (e.g., the auricle). Alternative versions can be worn on the body or a fully implantable system can be provided which incorporates the speech processor and/or microphone into the internal component assembly 144.

Internal component assembly 144 comprises an internal receiver unit 112, a stimulator unit 126 and an electrode assembly 118. Internal receiver unit 112 comprises an internal transcutaneous transfer coil (not visible in this view), and, in some embodiments, a magnet fixed relative to the internal coil. Internal receiver unit 112 and stimulator unit 126 are hermetically sealed within a biocompatible housing. The internal coil receives power and data from external coil 108, as noted above. A cable or lead of electrode assembly 118 extends from stimulator unit 126 to cochlea 132 and terminates in an array 134 of electrodes. Signals generated by stimulator unit 126 are applied by the electrodes of electrode array 134 to cochlea 32, thereby stimulating the auditory nerve 138.

While cochlear implant system 100 is described above as having external components, in alternative embodiments, cochlear implant system 100 can be a totally implantable prosthesis. In one exemplary implementation, for example, speech processing unit 116, including the microphone, speech processor and/or power supply can be implemented as one or more implantable components. In one particular embodiment, speech processing unit 116 can be contained within the hermetically sealed housing.

Figure 2:
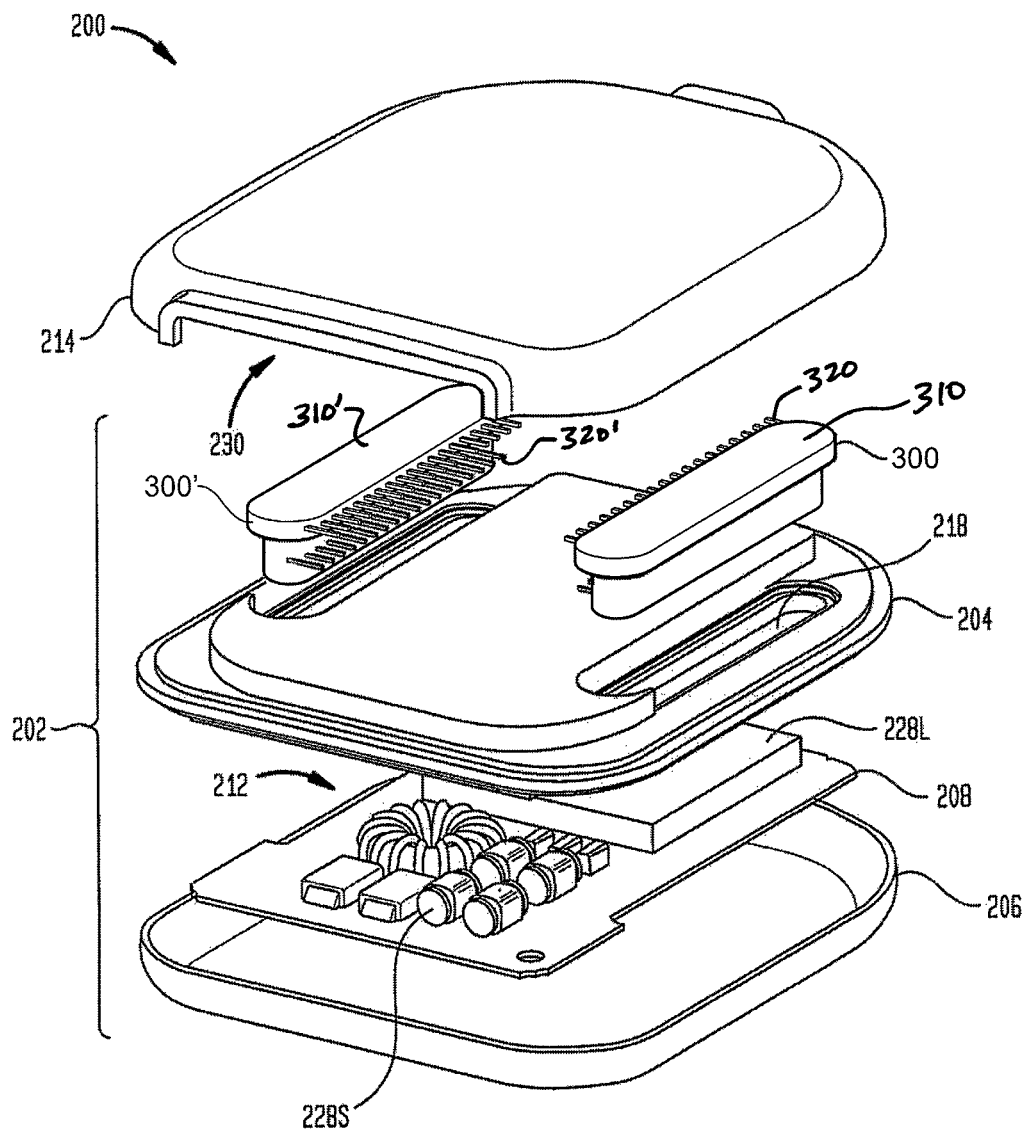
FIG. 2 is an exploded perspective view of a medical implant in accordance with embodiments of the present invention.

FIG. 2 is an exploded perspective view of an implantable component of an implantable medical device 200 in accordance with embodiments of the present invention. Implantable component 200 comprises a hermetically-sealed enclosure in the form of container 202. Hermetically-sealed container 202 is formed by a bottom shell 206 hermetically sealed to a chassis 204. Container 202 defines a hermetic enclosure in which functional components 212 are located. In the embodiment illustrated in FIG. 2, functional components 212 include a printed circuit board (PCB) 208 and electronic components 228 mounted on PCB 208. In certain embodiments, electronic components 228 may comprise one or more relatively large components 228L and one or more relatively small components 228S. In some embodiments, electronic components 228 may include a battery.

Container 202 further comprises two hermetic feedthroughs 300 and 300' disposed in apertures 218 of chassis 204. In the embodiment illustrated in FIG. 2, each of feedthroughs 300 and 300' includes an insulating body 302 and 302', respectively, and a plurality of electrical conductors 304 and 304', respectively. As will be discussed in greater detail below, each of the conductors includes a change in direction within the insulating body (in this particular case, a 180° change in direction). In certain embodiments, such a change in direction facilitates a reduction in the thickness of the implantable component. In some embodiments, electrical conductors 304 and 304' are configured to provide electrically conductive paths (e.g., electrical input/output lines) between components inside and outside of the hermetic enclosure of container 202 without degrading the hermetic seal of the enclosure. Instead of conductors 304 and 304', in some embodiments, feedthroughs 300 and 300' may include input/output lines that may be, for example, wires (formed from, e.g., copper, fiber optic, etc.), cables, tubes, etc., that facilitate the transfer of energy, data, materials, biological samples, etc., between functional components 212 and the recipient, other implants, external components, etc. In certain embodiments, each feedthrough includes at least one electrically conductive path extending through the feedthrough.

In the embodiment illustrated in FIG. 2, first ends of conductors 304 extend from PCB 208 to hermetic feedthrough 300 within the hermetic enclosure of container 202 and first ends conductors 304' extend from the bottom of PCB 208 to hermetic feedthrough 300' within the hermetic enclosure of container 202. Additionally, second ends of conductors 304 and 304' extend from feedthroughs 300 and 300', respectively, outside of the hermetic enclosure. Outside of the hermetic enclosure, second ends 304 and 304' may be electrically connected to different functional components of an implantable medical device. For example, in the exemplary cochlear implant described above with reference to FIG. 1, second ends of conductors 304 may be electrically connected to an internal transcutaneous transfer coil and second ends of conductors 304' may be electrically connected to electrode array 134. Hermetic feedthroughs 300, 300' allow for many input/output lines of any type to infiltrate enclosure 202, while maintaining the hermetic seal of the enclosure.

Additionally, a top shell 214 is connected to container 202 and defines an impact side of implantable component 200. In some embodiments, top shell 214 is not hermetically sealed to container 202. This enclosure is non-hermetic due to the presence of at least one aperture 230 through which leads are connected to other functional components of the implantable component, such as another implantable component or an electrode assembly. Top shell 214 comprises a lateral surface defining the top surface of implant 200, and side walls extending generally orthogonally from the lateral surface. Similarly, bottom shell 206 comprises a lateral surface defining the bottom surface of implant 200, and side walls extending generally orthogonally from the lateral surface. Top shell 214 and bottom shell 206 mate with opposing sides of a peripheral edge of chassis 204. It should be appreciated, however, that top and bottom shells 214, 206 can be coupled in a myriad of ways. In one alternative embodiment, for example, top and bottom shells 214, 206 directly mate with each other. The shells and hermetic enclosure can be formed of suitable biocompatible materials such as titanium, stainless steel or cobalt-chromium alloys, and can be joined using techniques such as laser welding or diffusion bonding.

The top shell 214 in combination with chassis 204 is typically designed to have a desired impact resistance and can be made thicker than the bottom layer in certain embodiments of the present invention. For example, the top layer can be formed of 0.4 mm thick titanium and the bottom layer of 0.2 mm thick titanium. In some embodiments, an inner filler material can be injected or inserted in the non-hermetic enclosure and/or hermetic enclosure to provide additional structural integrity or impact resistance. The exterior of the implant can be coated in silicone elastomer, epoxy or other protective coating.

Various embodiments of feedthrough 300, in accordance with certain embodiments of the present invention, are described below. FIG. 3A is a schematic diagram of a feedthrough 300 in accordance with certain embodiments of the present invention. FIG. 3A is a cross-sectional view of a feedthrough 300 having a square cross-sectional shape. In certain embodiments, feedthrough 300 is generally cube-shaped, while in other embodiments, feedthrough 300 may be generally shaped like a rectangular prism. Feedthrough 300 comprises an electrical insulator 310 having a first face 312 and second face 314 which is substantially perpendicular to first face 312. Feedthrough 300 also comprises an electrical conductor (or electrically conducting member) 320, referred to herein as conductor 320. A portion of conductor 320 disposed in insulator 310 includes a substantially 90 degree or substantially right angle bend 322 so that the non-linear conductor 320 enters first face 312 and exits second face 314, rather than exiting an opposite face 316 opposite entry face 312. As used herein, a "non-linear" conductor is a conductor that includes one or more curves or bends and well as one or more straight sections.

Accordingly, FIG. 3A shows a feedthrough comprising an insulator 310 and at least one conductor 320, the insulator 310 having an entry face 312 in which the at least one conductor 320 enters, and an exit face 314 from which the at least one conductor 320 exits, the exit face 314 being substantially perpendicular to the entry face 312.

FIG. 3A represents a cube shaped feedthrough 300. However, in accordance with certain embodiments of the present invention, feedthroughs (i.e., insulators 310 of feedthroughs 300) can be provided in a range of regular or irregular shapes. Some regular shapes include cubes, blocks, cylinders, spheres or other shapes with a constant cross-section, or in which the shape of the cross-section is constant but varies in absolute size as a function of length (e.g., tapers). FIGS. 3B to 3D illustrate certain embodiments of the present invention in which feedthrough 300 has the shape of a rectangular block, octagonal cylinder, and circular cylinder, respectively, each with a conductor 320 having a portion disposed in insulator 310 that including a 90 degree bend. In embodiments in which a feedthrough has a curved surface, the reference to a face should be taken to include a hypothetical surface which is tangential to a point of reference on the curved surface (typically the entry or exit point of the conductor). Moreover, in some embodiments in which a feedthrough has a curved surface, a "face" may include a surface of the insulator which lies in a plane that is tangential to the insulator at a location on the surface of the insulator at which a portion of the conductor extends out of the insulator.

FIGS. 4A to 4C illustrate various alternative embodiments of the feedthrough 300 of FIGS. 3A to 3D. FIG. 4A illustrates a feedthrough 300 which includes a conductor 320 having a portion disposed in insulator 310 that includes two 45 degree bends. FIG. 4B illustrates a feedthrough 300 which includes a curved conductor 320 wherein the portion of conductor 320 disposed in insulator 310 has a constant radius of curvature. FIG. 4C illustrates a feedthrough 300 which incorporates a curved conductor 320 in which a portion of conductor 320 disposed in insulator 310 curves through a 270 degree circular arc so as to provide an extended path length within the insulator 310.

Feedthrough arrangements described herein with reference to some embodiments of the invention may enable the production of thinner or more compact implantable components through a reduction in overall size of the feedthrough and associated connections. An example of such a reduction in size is illustrated in FIGS. 5A and 5B, which are schematic diagrams of implantable components of implantable medical devices illustrating a reduction in the headspace achieved through the use of a feedthrough 300 of FIG. 3A, in accordance with certain embodiments of the present invention. FIG. 5A illustrates a prior art hermetic enclosure 510 shown on the left with top surface 512 through which a conventional feedthrough 520 with a linear conductor 522 is provided. An external functional component 530 including conductor 532 having a 90 degree bend is connected to the upper end of linear conductor 522 at point 534. FIG. 5B illustrates hermetic enclosure 510 with a top surface 512 through which the feedthrough 300 of FIG. 3A (rotated 180 degrees with respect to FIG. 3A), in accordance with certain embodiments, is connected to exterior functional component 530 by straight conductor 536 which is connected to the upper end of conductor 320 at point 538. In some embodiments of the invention, by incorporating a 90 degree bend of conductor 320 within the insulator of feedthrough 320, a reduction 540 in the headspace above the hermetic enclosure can be achieved. In such embodiments, an additional advantage is that a size reduction may be achieved without compromising impact resistance of the device since it was not necessary to reduce the amount or the thickness of the implant material. A further advantage of the embodiment illustrated in FIG. 5B is that the top surface of the feedthrough is an insulator. Hence when a top shell is added (e.g., top shell 214 in FIG. 2) there is no need to add insulation between the conductor 320 and the top shell.

FIG. 5C illustrates an alternative hermetic enclosure 510, in accordance with some embodiments, in which the orientation of feedthrough 300 is reversed or inverted with respect to the orientation in FIG. 5B to illustrate connection of the feedthrough to a functional component 550 located within the hermetic enclosure. In this embodiment, the component 550 has a straight electrical conductor 552 which connects to the feedthrough conductor 320 at connection point 554. Such embodiments may be advantageous in that the bottom surface of the feedthrough 300 is an insulator (as opposed to having an exposed conductor, as illustrated in FIG. 5A) and hence there is no need for a separate insulation material between the conductor 320 and the bottom surface of the case 510, which may facilitate a reduction 560 in the thickness of the implant.

The above embodiments illustrate a feedthrough in which the conductor exits the feedthrough through an exit face substantially perpendicular to the entry face. However a range of alternative embodiments can be provided in which the exit face is a face other than the face opposite the entry face (i.e., is not substantially parallel to the entry face), or in which the conductor undergoes at least one change in direction within the insulator so that the conductor exits the insulator at an angle and direction different to the angle and direction of entry.

Figure 6A:
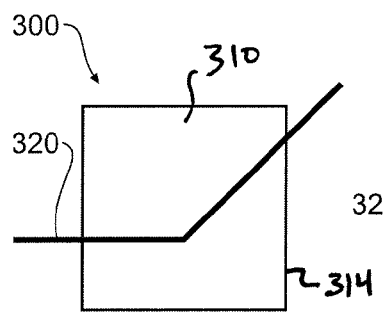
FIGS. 6A to 6I are schematic diagrams of various feedthroughs in accordance with embodiments of the present invention.
Figure 6B:
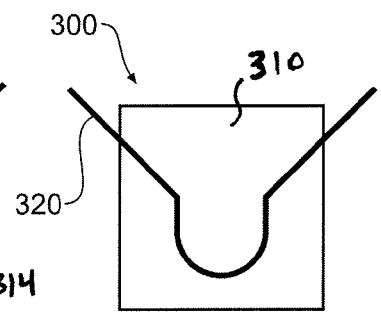
Figure 6C:
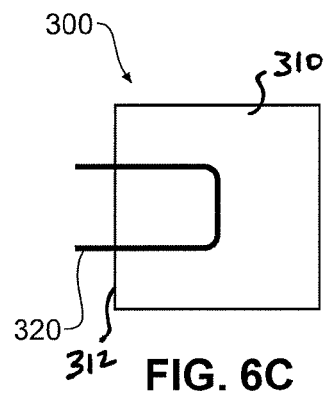

FIGS. 6A to 6I are schematic diagrams of embodiments of feedthrough 300 in accordance with certain embodiments of the present invention. In FIG. 6A, feedthrough 300 illustrates a 135 degree bend in a portion of conductor 320 disposed in insulator 310, so the conductor 320 exits at an (non-normal) angle with respect to the exit face. That is, in the embodiment of FIG. 6A, conductor 320 exits insulator 310 at an angle such that conductor 320 is not perpendicular to an exit face 314. In the embodiment illustrated in FIG. 6B, feedthrough 300 includes a looped conductor 320, with the looped portion disposed in insulator 310, such that the conductor 320 enters and exits at different angles with respect to the entry and exit faces. In the embodiment illustrated in FIG. 6C, feedthrough 300 includes a 180 degree bend in a portion of conductor 320 disposed in insulator 310, so that the conductor enters and exits from the feedthrough 300 on the same face (although with different directions). In such embodiments, since the entry and exit faces of insulator 310 are the same face, conductor 320 does not enter and exit opposite faces of insulator 310. As used herein, a "bend" of a specified number of degrees in a conductor may include one or more bends totaling the specified number of degrees. As will be described below, the lower part of such a feedthrough could form the sidewall of a hermetic enclosure. Additionally, in alternative embodiments, a conductor 320 that enters and exits from the same face of insulator 310 may include a portion disposed in insulator 310 having one or more bends totaling more or less than 180 degrees. For example, a portion of conductor 320 disposed in insulator 310 may include one or more bends totaling approximately 200 or totaling approximately 160 degrees. In such embodiments, conductor 320 may enter insulator 310 at an angle such that it does not enter perpendicular to a face 312, conductor 320 may exit insulator 310 at an angle such that it does not exit perpendicular to a face 312, or both.

Figure 6D:
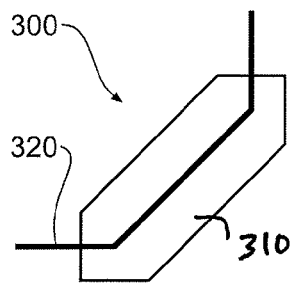
Figure 6E:
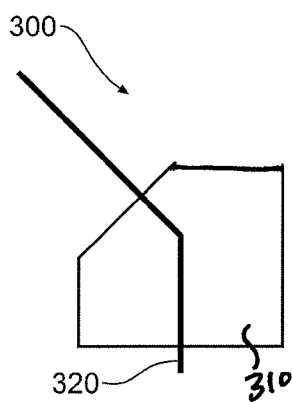
Figure 6F:
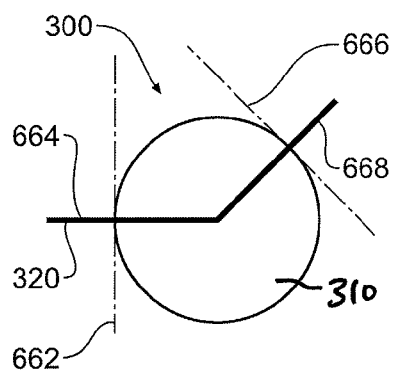
Figure 6G:
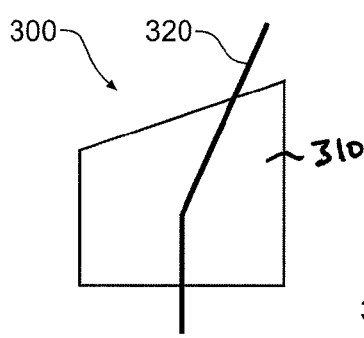
Figure 6H:
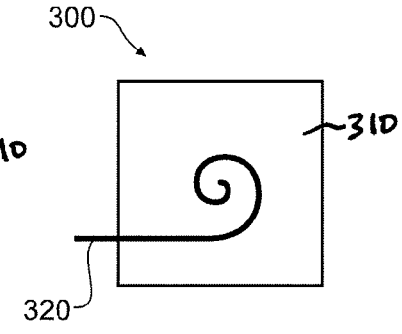
Figure 6I:
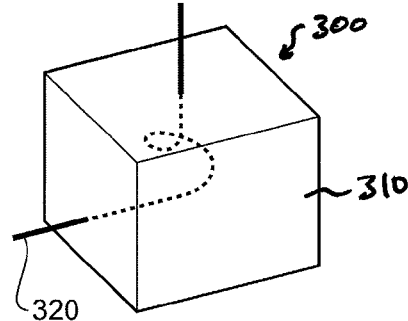

In the embodiment illustrated in FIG. 6D, feedthrough 300 is an inclined non-uniform hexagon, in which the portion of conductor 320 disposed in insulator 310 includes two 45 degree bends and enters and exits the first and third faces that are not opposite each other. In the embodiment illustrated in FIG. 6E, feedthrough 300 has an angled entry face and a portion of conductor 320 disposed in insulator 310 includes an internal direction change similar to that shown in FIG. 6A in which conductor 320 includes a 135 degree bend. In the embodiment illustrated in FIG. 6E, the exit face is inclined 45 degree with respect to the entry face so that the conductor 320 exits the inclined exit face at an angle normal (i.e., perpendicular) to the exit face (rather than at an inclined angle with respect to the exit face as in feedthrough 300 of FIG. 6A). In alternative embodiments, a total bend of more or less than 135 degrees may be used. In the embodiment illustrated in FIG. 6F, feedthrough 300 has a circular cross section and a portion of conductor 320 disposed in insulator 310 includes a 135 degree bend. In alternative embodiments, the portion of conductor 320 disposed in insulator 310 may include one or more bends imparting a change in direction totaling more or less than 135 degrees. As shown in FIG. 6F, an entry face of insulator 310 lies in a plane 622 that is tangential to a surface of insulator 310 where a first portion 664 of conductor 320 enters insulator 310. In addition, an exit face of insulator 310 lies in a plane 666 that is tangential to a surface of insulator 310 where a second portion 668 of conductor 320 exits insulator 310. In the embodiment illustrated in FIG. 6G, feedthrough 300 is a combination of the embodiments of feedthrough 300 illustrated in FIGS. 6A and 6E, in which the exit face is inclined with respect to the entry face and the conductor is inclined (non normal) with respect to the exit face, so that the conductor exits the insulator at an angle and direction different to the angle and direction of entry. In the embodiment illustrated in FIGS. 6H and 6I, feedthrough 300 includes a helical conductor 320 having a helical portion disposed in insulator 310 and a long path length inside insulator 310. In this embodiment, the conductor 320 exits insulator 310 through an exit face substantially perpendicular to the entry face. FIG. 6I shows a perspective view of the embodiment of feedthrough 300 shown in of FIG. 6H.

In the embodiments described above with reference to FIGS. 3A to 6I, each of feedthroughs 300 includes a single electrically conductive path provided by a conductor. However, each of these embodiments may include a plurality of conductors, configured in a manner similar to the illustrated conductor, providing a plurality of independent electrically conductive paths. In certain embodiments, each of the conductive paths may be formed by a unitary conductor. Additionally, in certain embodiments, the conductors may enter the insulator through the same or different faces and may exit the insulator through the same or different faces, or a combination thereof. In certain embodiments, when conductors enter or exit through different faces, the different faces may be parallel to one another.

FIGS. 7A to 7D are schematic diagrams of feedthroughs comprising a plurality of conductors in accordance with embodiments of the present invention. In the embodiment illustrated in FIG. 7A, feedthrough 300 has an octagonal cross section and includes a first conductor 320 entering a first face 711 of insulator 310, and a second conductor 320' entering an adjacent second face 718, with both conductors 320 and 320' exiting through a third face 714 (opposite the second face). In the embodiment illustrated in FIG. 7B, feedthrough 300 comprises a first conductor 320 entering a first face 721 of insulator 310 and a second conductor 320' entering a second face 723 opposite the first face, where both conductors 320 and 320' exit through a third face 725 which is substantially perpendicular to both the first and second faces.

In the embodiment illustrated in FIG. 7C, feedthrough 300 has three conductors 320, 320' and 320", each of which exits the feedthrough through an exit face substantially perpendicular to the entry face. Each of the conductors is located within a different parallel plane through the insulating body (and which are evenly distributed along a first axis of the insulating body). In this embodiment the entry points are each located on the same midline axis 732 of the entry face and the exit points are each located on the same midline axis 734 of the exit face. In the embodiment illustrated in FIG. 7D, feedthrough 300 is an alternative embodiment. In this embodiment three conductors 320, 320' and 320", each enter the feedthrough 300 along a central midline 732 of the entry face and exit the feedthrough 300 through an exit face substantially perpendicular to the entry face. However in this embodiment, the conductors have different path lengths within the insulator so that the exit points are not all located on the midline axis 734 of the exit face.

The feedthroughs described herein in accordance with embodiments of the present invention can be formed from a variety of materials and manufactured using a variety of methods. In certain embodiments, the insulating body of a feedthrough is bonded chemically at its perimeter to the walls of a hermetic enclosure through brazing or the use of oxides, and/or mechanically bonded through compression. The choice of material and manufacturing method to use will depend to some degree on the required shape, configuration and material used to construct the medical implant and/or conductor and insulator. In the case of brazing, materials should be chosen with appropriate thermal coefficients to prevent excessive differential expansion that can occur between the conductor and insulating body.

The electrical conductor (or conductors) can be formed from any suitable conductive material including conductive metal or alloys. The conductor can be a unitary conductor or formed from multiple members or parts. Exemplary conductive metals include transition metals (e.g. noble metals), rare-earth metals (e.g. actinide metals and lanthanide metals), alkali metals, alkaline-earth metals, and rare metals. Noble metals include gold (Au), platinum (Pt), palladium (Pd), niobium (Nb), and iridium (Ir). Exemplary alloys include platinum-gold, platinum-iridium, silver-palladium, gold-palladium or mixtures thereof, tungsten-Mo. Conductive material can be in the form of a paste (e.g. refractory metallic paste, metallic alloy paste, etc.), powder, or other suitable form. In some embodiments the conductor 320 can be provided in the form of a platinum wire (or platinum alloy) with a diameter of approximately 100m. The wire can be coated with epoxy or other plastics or waxes to further insulate the wire.

The electrical insulator 310, or insulating body (or member) can be a ceramic; glass or sapphire. Suitable ceramics include aluminum oxides, zirconium oxides, and magnesium oxides. The insulator 310 can be formed from one or more ceramic green sheets, binders, or other materials, which can be assembled and cured by firing to achieve a hermetic seal. Alternatively deposition or molding techniques can be used as discussed below.

FIGS. 8A to 8E are schematic diagrams of a method for forming a feedthrough 300 according to one embodiment. This method is suitable for feedthroughs in which the electrical pathway is formed from multiple conductors (i.e. a non-unitary conductor). An insulator 310 in the form of a block of ceramic is obtained and a first drilling step (FIG. 8A) is performed to form a first conduit 812 having an opening 814 in a first face 816, and an opening 818 in the opposite face (the conduit passing completely through the insulator 310). In other embodiments the conduit is drilled to a specific or predetermined depth so that there is no opening in the opposite face. A second drilling step (FIG. 8B) is then performed to form a second conduit 822 having an opening 824 in a second face 826, and which intersects the first conduit at an intersection point 828. In this embodiment the second face is substantially perpendicular to the first face and the conduits are drilled normal to the faces so that the conduits intersect at an angle of about 90 degrees. In alternative embodiments, the conduits may intersect at an angle other than 90 degrees.

Figures 8A, 8B:
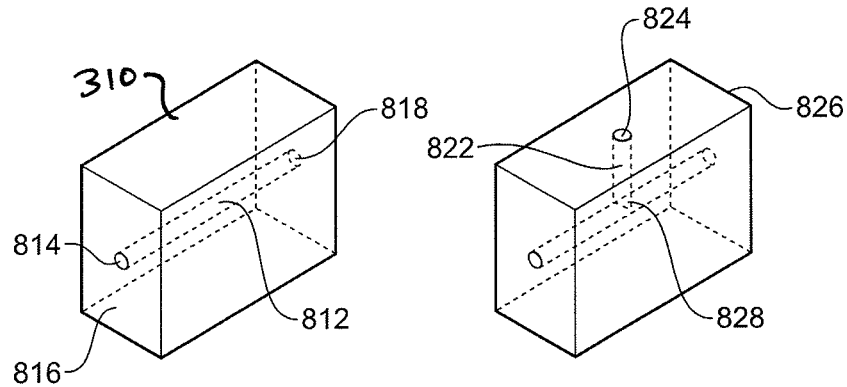
FIGS. 8A to 8E are schematic diagrams of a method for forming a feedthrough in accordance with embodiments of the present invention.
Figures 8C, 8D:
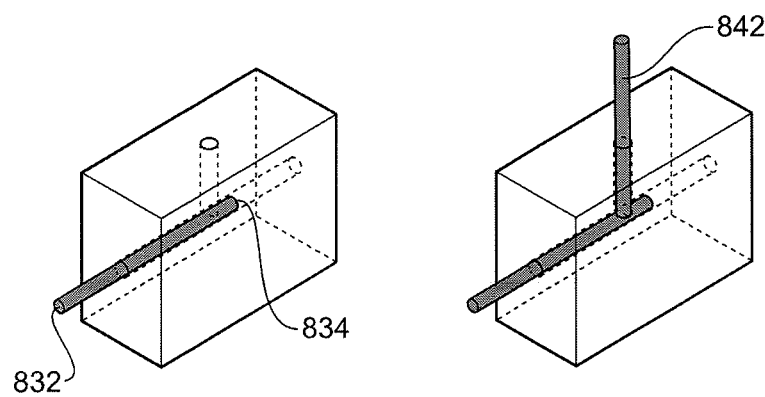
Figure 8E:
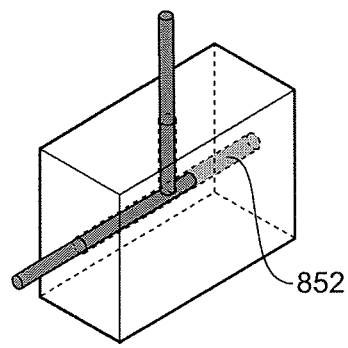

An electrical pathway is then formed between the opening in the first face and the opening in the second face by mechanically inserting a first linear conducting member 832 into the first linear conduit 812 (see FIG. 8C) and inserting a second linear conducting member 842 into the second linear conduit 822 until they intersect and form an electrical connection (see FIG. 8D). In one example, the linear conducting members are platinum wires. The steps for forming an electrical pathway are illustrated in FIGS. 8C to 8E with the first insertion step (FIG. 8C) comprising pushing a first wire 832 into the first conduit 812 past the point of intersection 828 and to a point 834 approximately three quarters along the length of the conduit. A second insertion step (FIG. 8D) is then performed in which a second wire 842 is inserted into the second conduit until it contacts the first wire at the point of intersection 828, thereby forming an electrical pathway between the first opening 814 and second opening 824. A backfilling step (FIG. 8E) is performed to fill the remaining empty space in the first conduit with a suitable non-conductive filling agent such as a ceramic gel/suspension 852. The ceramic can then be sintered such that the ceramic shrinks to form a bond with the conductors and that the filling agent fuses with the bulk ceramic.

Figure 12:
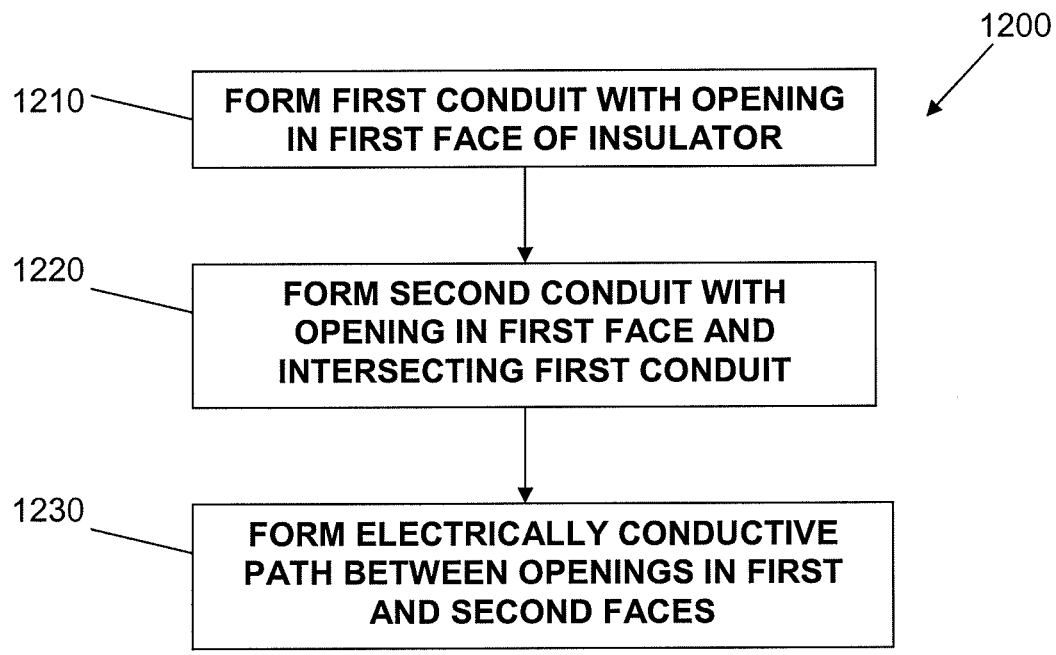
FIG. 12 is a flowchart of a method of forming a feedthrough in accordance with embodiments of the present invention.

FIG. 12 shows a flowchart 1200 of the above described method for forming a feedthrough. The method comprises, at block 1210, forming a first linear conduit in an insulator (or insulating member) in which the first linear conduit has an opening in a first face of said insulator. At block 1220, a second linear conduit is formed in the insulator such that the second linear conduit intersects the first linear conduit. In one embodiment the second linear conduit has an opening in a second face substantially perpendicular to the first face. In another embodiment the second linear conduit has an opening in a second face, which is a face other than the face opposite the first face. In another embodiment the second linear conduit enters the insulating body at an angle and direction different to the angle and direction of entry of the first linear conduit. At block 1230, an electrically conductive path between the opening in the first face and the opening in the second face is formed. In one embodiment this is performed by inserting a first linear conducting member into the first linear conduit and inserting a second linear conducting member into the second linear conduit. Other embodiments and variations on this method are also possible.

In one alternative embodiment the first wire is only inserted to the point of intersection. In another embodiment the first wire is inserted to a point between the point of intersection and the opening opposite the first opening 818 (see FIG. 8A). In another embodiment the wire is pushed entirely through the insulator. In another embodiment in which the conduit does not pass entirely through the insulator and ends within the insulator, the wire is inserted until it reaches the end of the conduit. In another embodiment the second conduit passes all the way through the insulator and the backfilling step further includes backfilling the empty space in the second conduit.

In another embodiment an electrically conductive path can be formed by a first wire, a braze material or electrically conducting paste, and a second wire. In this embodiment the braze material or electrically conducting paste acts to improve the reliability of the electrical connection between the first and second wire. Braze is melted or braze paste is inserted or electrically conducting paste is inserted (or poured) into the second conduit after the first wire has been inserted. The second wire is then inserted and the braze is heated and allowed to solidify or paste allowed to harden or solidify. Alternatively the braze material or paste can be first inserted into the conduits, and then each wire inserted and the braze heated or paste allowed to harden.

These approaches can also be extended to provide feedthroughs with a range of complex shapes or with angles other than 90 degrees. For example the feedthrough arrangement illustrated in FIG. 4A could be produced through drilling three conduits, namely a vertical conduit, a horizontal conduit and a third conduit inclined at 45 degrees which intersects the first and second conduit. Alternatively the second face could be inclined (or angled) with respect to the first face, or the conduits could be inclined (or angled) with respect to the surface they are drilled into. Conduits can be formed by other techniques such as the use of lasers or chemicals to ablate etch or otherwise form a suitable conduit. The hermetic seal can be generated through mechanical compression as the conductors are inserted, or further chemical treatment can be performed to form chemical bonds between the conductor and the insulating body. In the case of mechanical sealing, the dimensions of the conduit are matched to those of the conductor.

In another embodiment the feedthrough is formed from multiple layers of insulators and conductors using a combination of deposition and etching techniques similar to those used in fabrication of printed circuit boards and integrated circuits. A feedthrough can be formed from multiple layers of ceramic materials (such as ceramic green-sheet) into which a series of openings or channels are formed within which a conductive material can be located. In one embodiment, an insulating layer is formed from deposition onto a substrate, such as by using ion enhanced evaporated sputtering of aluminum oxide.

A metalized trace is then deposited onto the upper surface of the insulating layer using conventional deposition techniques as are known in the art. This trace can start at one edge and end in the middle of the insulating layer. A second insulating layer having an upper surface and lower surface is then deposited over the conductive material and the first insulating layer using conventional deposition techniques. The conductive material is thus sandwiched between the lower surface of the second insulating layer and the upper surface of the first insulating layer, thereby encapsulating the trace of conductive material within insulating material.

An opening is then formed through the second insulating layer to expose the end of the trace of conductive material. This second layer can be formed using conventional semiconductor processing techniques. For example, portions of the first insulating layer and/or trace of conductive material can be masked as the second insulating layer is sputtered (or otherwise deposited) onto the first insulating layer and conductive material. Depending upon the required thickness, additional top insulating layers can be added with aligned openings (so as to form a vertical pipe). The opening is then filled with a suitable conductive metal, such as platinum or tungsten to form a feedthrough with a 90 degree change in direction (e.g., as shown in FIG. 3A). Wires or leads can be inserted into the opening or connected to the conductive trace at the edge of the feedthrough if required.

The deposition of insulating layers acts to encapsulate and hermetically seal the conductive trace. The hermeticity of the feedthrough can be increased by creating serpentine or convoluted paths through the feedthrough. This can be achieved using a combination of multiple layers, openings and traces, in which some of the openings only pass through some of the layers and conductive traces can be laid down to join such openings.

Figure 13:
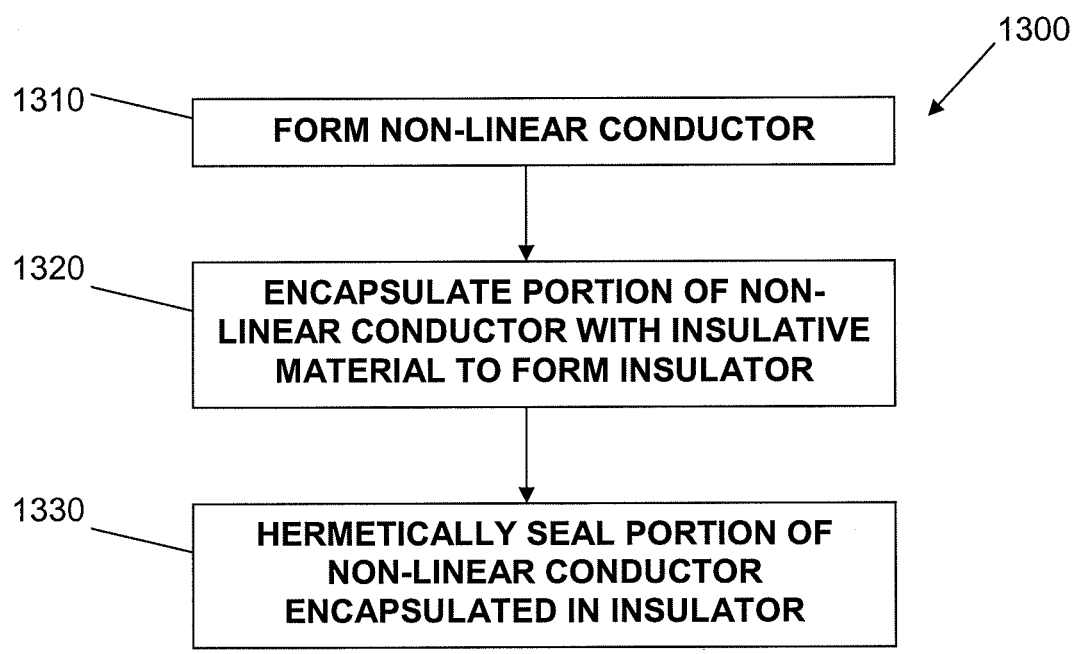
FIG. 13 is a flowchart of another method of forming a feedthrough in accordance with embodiments of the present invention.

In another embodiment a feedthrough is formed by encapsulating a portion of a non-linear conductor with an insulating material. A flowchart 1300 of this method is illustrated in FIG. 13. At block 1310, one or more non-linear conductors are formed. In certain embodiments, each of the non-linear conductors may be formed with the shape of any one of the conductors described in relation to the embodiments discussed above. At block 1320, a portion of each of the one or more non-linear conductors is encapsulated with an insulating material to form a contiguous insulating body (or insulator) which circumferentially covers said portion of each of the one or more non-linear conductors. In certain embodiments of the present invention, the insulating material can be coated, molded or bonded around the conductors to form the contiguous insulating body. Additionally, in some embodiments, a non-linear portion of the conductor is encapsulated with the insulating material.

In certain embodiments, a forming step may be performed on the insulating body to form or mould the shape of the insulating body. The insulating material can be formed or molded into an insulating body with a defined shape such as cylinder, cube, block or it can be an irregular shape. In one embodiment the exit face is substantially perpendicular to the entry face. In another embodiment the exit face is a face other than the face opposite the entry face. In another embodiment the non-linear conductor exits the insulating body at an angle and direction different to the angle and direction of entry. In some embodiments, the forming step may be performed concurrently with encapsulating the non-linear conductors with insulative material at block 1320.

At block 1330, a hermetic seal is formed around the encapsulated portion of each of the one or more non-linear conductors by the contiguous insulating body. In certain embodiments, the encapsulated portion of each of the non-linear conductors is hermetically sealed within the insulator. In some embodiments, the hermetic seal is formed by sintering the conductors and the insulating body. Also, in some embodiments, the conductor is a unitary conductor. In other embodiments, the conductor is formed from conductive elements suitably integrated to each other, such as, for example, conductive elements integrated via the sealing process (such as sintering).

In one embodiment the feedthrough is formed by first obtaining a conductor having a desired non-linear shape. In one embodiment a linear section of platinum wire is bent into the desired non-linear shape (e.g. given a 90 degree bend). In another embodiment the desired shape is formed by removal of material from a sheet or a film of platinum (or other suitable metal or alloy). This removal step can be performed using a punch out technique, electrical discharge machining (EDM), micro knifing, and/or laser cutting. In one embodiment the conductor is formed using molding techniques. One such molding technique is metal injection molding (MIM) in which a metal powder and binders are mixed and homogenized to create feedstock. The feedstock is then molded into a desired structure. The presence of the binder serves to make the feedstock sufficiently fluid to be used in injection molding process. Once molded the structure is allowed to set, and then undergoes debinding and sintering to hermetically seal the insulator around the conductor. Complex three dimensional shapes can be formed using this process.

In certain embodiments, the conductor is formed from a sacrificial component and a non-sacrificial component. In certain embodiments, at least a portion of the non-sacrificial component is encapsulated by an insulative material, such as by coating the portion or using a mold. The sacrificial component is left untouched and then at least a portion of the sacrificial component is removed. The green body of the insulator can undergo debinding and sintering, which leads to shrinking of the ceramic and formation of a hermetic seal around the conductor. The ceramic feedthrough can then be mounted into a medical implant. This embodiment is particularly useful in cases where the feedthrough is required to have multiple independent pathways, as a plurality of unitary conductors can initially be joined via a common sacrificial component. For example, a sheet of conductive material could be obtained and etched or cut so that a plurality of non sacrificial components of the desired shaped are joined by one or two sacrificial components located at either end of the non-sacrificial components. Following encapsulation, removal and sintering a feedthrough with multiple independent electrically conductive paths is obtained.

In certain embodiments, the insulating body can be formed using a molding process, such as powder injection molding (PIM) which is similar to MIM discussed above. In such embodiments, a suitable fine ceramic power is mixed with binder and molded around the desired portion of the conductor. The mold is allowed to at least partially set to form a green body. Once the green body is set, the sacrificial component can be removed, such as by the use of laser cutting. The green body can then undergo debinding and sintering to hermetically seal the insulator around the conductor.

Complex arrangements or shapes can be produced through multiple molding. For example, in the case of a helix, the conductor could be wound around a screw-like helical a support structure, and insulating material could be molded around the exterior and allowed to set, the support structure could then be removed (e.g. unscrewed) and the cavity filled with further insulative material which is allowed to set. Sintering will then form the insulating material into a single unitary insulating body.

Figure 9:
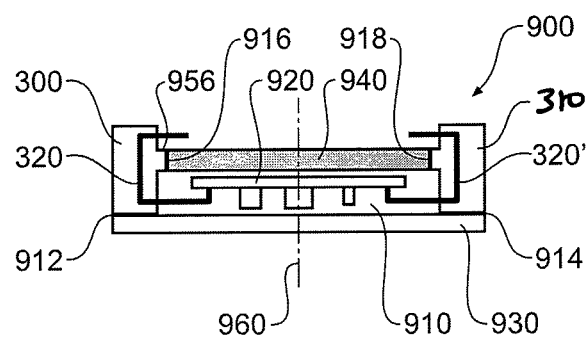
FIG. 9 is a schematic view of a hermetic enclosure of a medical implant including a feedthrough in accordance with embodiments of the present invention.

FIG. 9 is a cross-sectional schematic view of substantially disc-shaped hermetic enclosure for a medical implant 900 including a feedthrough having at least one conductor with a 180 degree bend in accordance with certain embodiments of the present invention. A hermetic enclosure 910 including functional components 920 is formed from a base 930 and a top 940 which are sealed to an annular feedthrough 300 to provide a substantially disc shaped implant with an axis of rotation 960. The feedthrough includes multiple conductors 320, 320', each of which are connected to functional components located within the hermetic enclosure. As shown in FIG. 9, the respective portions of conductors 320 and 320' disposed in insulator 310 of the feedthrough each include a plurality of bends totaling a 180 degree change in direction through insulator 310. As shown each conductor 320 and 320' exits insulator 310 just above the upper surface of the top 940. The side wall of the hermetic enclosure is formed by the feedthrough 300. In certain embodiments, feedthrough 300 including conductors 320 and 320' each including a 180 degree change in direction allows the stack height of the implant to be reduced. In some embodiments, base 930 and top 940 are titanium, feedthrough 300 is brazed to base 930 and top 940 at surfaces 912, 914, 916, and 918 using standard production techniques to create a hermetic seal. To assist with the mating and alignment of feedthrough 300 with top surface 920, feedthrough 300 includes a projection 956. This feature also aids assembly of the top 940 past the conductors 320, 320' which can be temporarily bent upwards during assembly.

Figure 10:
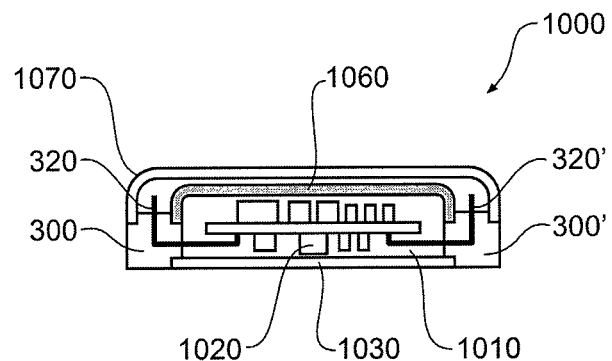
FIG. 10 is a cross-sectional view of a medical implant including a feedthrough in accordance with embodiments of the present invention.

FIG. 10 is a cross-sectional view of a medical implant 1000 including a feedthroughs 300 and 300' each having at least one conductor with a 90 degree bend in accordance with certain embodiments of the present invention. A hermetic enclosure 1010 including functional components 1020 is formed from a base 1030 and a top 1060 which are hermetically sealed to feedthroughs 300 and 300'. A cover 1070 is joined to the outer top corners of each of feedthroughs 300 and 300' to form the exterior of the implant. In this embodiment, top 1060, base 1030 and cover 1070 are formed from titanium and are joined and sealed to feedthroughs 300 and 300' using brazing. Each of feedthroughs 300 and 300' includes one of conductors 320and 320', respectively, each of which includes a 90 degree bend within the feedthrough to exit into the channels formed between the inner side of cover 1070 and the outer side of the top 1060 of the hermetic enclosure 1010. In the embodiment illustrated in FIG. 10, the portions of conductors 320 and 320' disposed in the respective insulators of feedthroughs 300 and 300' include the 90 degree bend. In other embodiments, the bend may have an angle other than 90 degrees.

In the embodiments illustrated in FIGS. 9 and 10, reductions in the stack height are achieved by providing one or more bends in the portion of the conductor disposed within the insulator of the feedthrough. In each of these embodiments, the conductors enter the feedthrough in substantially the same plane as the functional components, and exit the feedthrough either at the top of the feedthrough (i.e. in a different plane) or such that the conductors extend over the functional components, resulting in a reduction in the overall size of the medical implant. Again, the reduction in size has been achieved without compromising impact resistance or structural integrity. In certain embodiments, providing conductors having one or more bends within the insulator of the feedthrough allows the stack height to be reduced without reducing the size of the insulator, which may be beneficial since the ability of the feedthrough to provide a hermetic seal may be dependent upon the length of the contact between the insulator and the conductor within the feedthrough.

Figure 11:
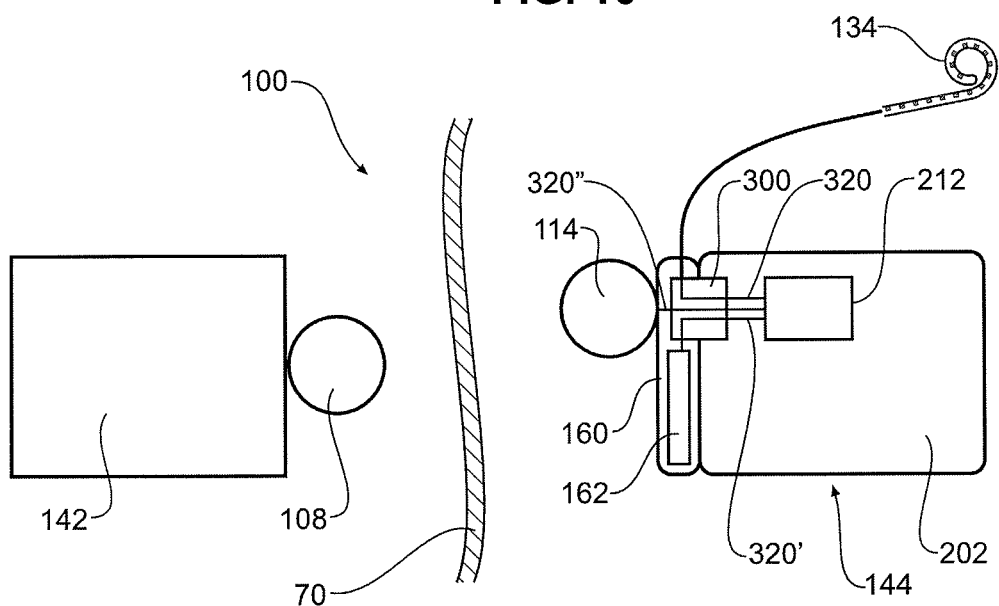
FIG. 11 is a schematic illustration of a cochlear implant system including a feedthrough in accordance with embodiments of the present invention.

FIG. 11 shows a medical implant system 100, namely a cochlear implant system, including an external component assembly 142, including a sound processor, and an implantable component assembly 144, being a stimulator, implanted into an recipient under tissue 70, in accordance with embodiments of the present invention.

In the illustrated embodiment of FIG. 11, processor 142 receives input signals in the form of sound information from the surrounding area around the recipient via any suitable means, such as a microphone (not shown) and processes this data into control signals for transmission to the implantable component assembly or stimulator 144. The control signals are transmitted transcutaneously across tissue 70 via transmitting coil 108, to be received by receiving coil 114 of the stimulator. The control signals are then further processed by the functional components 212 located within the hermetic container 202 (enclosure) in the stimulator 144, to provide stimulation signals for applying directly to the cochlea of the recipient via electrode array 134 as will be understood by the person skilled in the art. A housing 160 includes a replaceable battery 162 for providing power to the stimulator 144.

A feedthrough 300 is provided to provide electrically conductive paths between the functional components 212 located in the hermetic container 202 and the electrode array 134, receiver coil 114 and battery 162, located outside of hermetic container 202, via conductors 320, 320' and 320" respectively. Conductors 320 and 320' each undergo a substantially 90 degree change in direction within the insulator of the feedthrough and exit the feedthrough through to top and bottom faces (being faces substantially perpendicular to the side entry face).

Certain embodiments of the present invention allow for the design and manufacture of implantable components of implantable medical devices of reduced size compared to those having conventional feedthrough arrangements. Further these reductions in size can be achieved while substantially maintaining existing hermeticity and strength of conventional implants. In certain embodiments, relatively long path lengths can be provided in more compact feedthroughs providing smaller feedthroughs without detrimentally shortening the length of the contact between conductors and the insulators in which they are disposed. Thinner implantable components may be desirable for cochlear implants where there is limited space between skull and skin for the implantation of the implantable component.

Further, in certain embodiments, by providing feedthrough arrangements in which the conductor is allowed to bend, or undergo a change in direction of the path (i.e. from a linear path) whilst within the feedthrough, greater flexibility is provided in the overall design of the medical implants. For example the conductors can enter the feedthrough in the same plane as the functional components, but can be selected to exit at a convenient point which allows a reduction in the size of the implant as the exit point is not limited to being in line with the entry point (i.e. can be on a different face or angle). Further, in some embodiments, a feedthrough can be designed to form the sidewall of a hermetic enclosure of an implantable component. This design flexibility allows for a reduction in the headspace or overall size of the implantable component.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. The present embodiments are, therefore, to be considered in all respects as illustrative and not restrictive.

What is claimed is:

1. An implantable medical device comprising:
a hermetic enclosure including at least one feedthrough having at least one electrically conductive path through the feedthrough, the at least one feedthrough comprising:
an insulator having an entry face and an exit face; and
at least one non-linear conductor configured to extend, within the insulator, from the entry face to the exit face to provide the conductive path, wherein the entry and exit faces are not substantially parallel opposite faces of the insulator;
wherein the hermetic enclosure further includes a first metal housing member and a separate second housing member, with an outer sidewall of the enclosure extending between and connecting the first and second metal housing members to hermetically seal the hermetic enclosure, wherein the outer sidewall is defined by the insulator of the feedthrough.

2. The implantable medical device of claim 1, wherein the entry face is substantially perpendicular to the exit face.

3. The implantable medical device of claim 1, wherein the entry face and the exit face are the same face of the insulator.

4. The implantable medical device of claim 3, wherein a portion of the conductor disposed in the insulator includes a 180-degree bend.

5. The implantable medical device of claim 1, wherein the insulator is substantially cylindrical and the entry face lies in a plane tangential to the insulator at a location on the surface of the insulator at which a first portion of the conductor extends out of the insulator.

6. The implantable medical device of claim 5, wherein the exit face lies in a plane tangential to the insulator at a second location on the surface of the insulator at which a second portion of the conductor extends out of the insulator.

7. The implantable medical device of claim 1, wherein a portion of the conductor disposed in the insulator comprises one or more bends.

8. A cochlear implant system comprising:
an electrode array; and
an electronics module comprising a hermetic enclosure encasing one or more functional components and including at least one feedthrough having at least one electrically conductive path through the feedthrough configured to electrically connect the functional components to the electrode array, the at least one feedthrough comprising:
an insulator having an entry face and an exit face; and
at least one non-linear conductor configured to extend, within the insulator, from the entry face to the exit face to provide the conductive path, wherein the entry and exit faces are not substantially parallel opposite faces of the insulator;
wherein the hermetic enclosure comprises a first metal housing member and a separate second housing member, with an outer sidewall extending between and connecting the first and second metal housing members to hermetically seal the hermetic enclosure, wherein the outer sidewall is defined by the insulator of the feedthrough.

9. The system of claim 8, further comprising:
an external component configured to receive input signals and convert the received input signals into control signals; and
an implantable component configured to receive the control signals from the external component, wherein the internal component comprises the electrode array and the electronics module.

10. The system of claim 8, wherein a portion of the conductor disposed in the insulator comprises one or more bends.

11. The system of claim 8, wherein the entry face is substantially perpendicular to the exit face.

12. The system of claim 8, wherein the entry face and the exit face are the same face of the insulator.

13. The system of claim 12, wherein a portion of the conductor disposed in the insulator includes a 180degree bend.

14. The system of claim 8, wherein the first metal housing member comprises a base, wherein the second metal housing member comprises a top, and wherein the insulator includes the outer sidewall and a projection extending inwardly from the outer sidewall, wherein the projection is configured to be mated and aligned with the top of the hermetic enclosure.

15. A method of forming a feedthrough and a hermetic enclosure for an implantable medical device, the method comprising:
forming at least one non-linear conductor;
encapsulating a portion of the non-linear conductor with an insulating material to form a contiguous insulator having entry and exit faces that are not substantially parallel opposite faces of the insulator, wherein that the non-linear conductor is configured to extend, within the insulator, from the entry face to the exit face;
hermetically sealing the portion of the non-linear conductor encapsulated in the insulator; and
forming a hermetic enclosure comprising a first metal housing member and a separate second metal housing member, with an outer sidewall extending between and connecting the first and second metal housing members to hermetically seal the hermetic enclosure, wherein the outer sidewall is defined by the insulator of the feedthrough.

16. The method of claim 15, wherein said hermetically sealing the portion of the non-linear conductor within the insulator includes sintering the insulator and the non-linear conductor.

17. The method of claim 15, wherein, after encapsulating the portion of the non-linear conductor, the insulator circumferentially surrounds the portion of the non-linear conductor.

18. The method of claim 15, wherein the entry face is substantially perpendicular to the exit face.

19. The method of claim 15, wherein the entry face and the exit face are the same face of the insulator.

20. The method of claim 19, wherein the portion of the conductor encapsulated within the insulator includes a 180 degree bend.

21. The implantable medical device of claim 3, wherein the first metal housing is connected to the insulator at the same face of the insulator where the conductive path enters and exits the insulator.

22. The implantable medical device of claim 21, wherein the first metal housing is connected to a protrusion of the insulator at the same face of the insulator where the conductive path enters and exits the insulator.

23. The implantable medical device of claim 21, wherein the first metal housing is connected to the insulator at the same face of the insulator where the conductive path enters and exits the insulator and between where the conductive path enters and exits the insulator.

24. The implantable medical device of claim 23, wherein the conductive path changes in direction by at least 180 degrees as the conductive path extends through the insulator.

25. The implantable medical device of claim 1, wherein the outer sidewall is annular such that the hermetic enclosure is substantially disc shaped.

26. The implantable medical device of claim 1, wherein the outer sidewall connects to the first and second metal housing members at braze connections.

27. The implantable medical device of claim 1, further comprising a cover extending over the exit face of the feedthrough.

28. The implantable medical device of claim 27, wherein the cover comprises a metal cover joined to the insulator of the feedthrough.

* * * * *